United States Patent [19]

Mewburn

[11] Patent Number: 5,443,082
[45] Date of Patent: Aug. 22, 1995

[54] CONTROLLING ARTICLES OF EQUIPMENT DURING SURGERY

[75] Inventor: Judith J. Mewburn, London, England

[73] Assignee: British Technology Group Ltd., London, England

[21] Appl. No.: 927,485
[22] PCT Filed: Apr. 2, 1991
[86] PCT No.: PCT/GB91/00511
§ 371 Date: Sep. 28, 1992
§ 102(e) Date: Sep. 28, 1992
[87] PCT Pub. No.: WO91/15159
PCT Pub. Date: Oct. 17, 1991

[30] Foreign Application Priority Data

Mar. 30, 1990 [GB] United Kingdom .................. 9007197

[51] Int. Cl.⁶ .............................................. A61B 19/00
[52] U.S. Cl. ...................................................... 128/897
[58] Field of Search ................................. 128/897–899

[56] References Cited

U.S. PATENT DOCUMENTS 4,039,827 8/1977 Zdrok et al. .......................... 250/271
4,978,335 12/1990 Arthur, III .................... 128/DIG. 1
5,031,642 7/1991 Nosek ................................... 604/317

FOREIGN PATENT DOCUMENTS 3917876 12/1990 Germany .
2069842 9/1981 United Kingdom .
2216259 10/1989 United Kingdom .

OTHER PUBLICATIONS

WO, A, 8909563 (Pollock et al.) 19 Oct. 1989 see page 1, last paragraph–page 3, paragraph 1; FIGS. 1, 2.

Primary Examiner—William E. Kamm
Assistant Examiner—J. P. Lacyk
Attorney, Agent, or Firm—Cushman, Darby & Cushman

[57] ABSTRACT

Articles of equipment such as swabs and surgical instruments are provided with a machine readable information source such as a bar code, and are monitored during surger by means of a system which comprises a bar code scanner (19) and a computer (3) on which information read by the scanner can be stored. The system may include scales (9) for weighing the equipment so that body fluid absorbed by absorbent articles such as swabs can be determined.

16 Claims, 2 Drawing Sheets

CONTROLLING ARTICLES OF EQUIPMENT DURING SURGERY

BACKGROUND OF THE INVENTION

1. Field of the Invention

The present invention relates to a system for controlling articles of equipment for use in surgery, and to a method of controlling such articles during surgery.

2. Description of the Related Art

Care must be taken during surgery performed on human or animal bodies to ensure that no article of equipment which is used during the surgery is left unintentionally in a cavity in the body of the human or animal. A Code of Practice overseen by the UK Central Council governs procedures which are used in hospitals in the United Kingdom to control equipment used in surgery. Such equipment includes swabs, sutures and surgical instruments. The procedures involve two nurses who are required to count the articles of equipment manually, and to write a list of the counted articles on a wall board. After surgery has been completed, repeated checks are made to ensure that all articles of equipment which were counted before surgery can be found.

Certain articles of equipment are used to absorb body fluids' which are lost during surgery. Generally such fluid is blood. It can be desirable to monitor the degree of fluid loss during surgery and for this reason, the articles of equipment formed from absorbent material are commonly weighed before and after use. Accurate calculation of the amount of body fluid which has been lost obviously requires accurate identification of the article in question so that its weight before use can be determined. As part of the counting procedure, it is common for articles of absorbent material to be stored on a rack after use: a risk of infection is associated with this technique, because of the tendency of the absorbed body fluids to be released from the articles while on the rack.

GB-A-2069842 discloses a method of detecting surgical swabs such as spones used to absorb body fluids during surgery. The swabs are impregnated with a heavy metal salt such as barium sulphate, and the method involves exposing the patient to X-rays which are absorbed directly by the salt. This document does not ad dress the problem of controlling articles such as swabs during surgery. It does however recognise the problems which can a rise through inaccurate control and to minimise those problems, it suggests a technique which involves exposure of a patient to X-rays.

It is, of course widely recognised that unnecessary exposure of patients to X-rays should be avoided.

SUMMARY OF THE INVENTION

The present invention provides a technique for controlling articles of equipment for use in surgery, through automation of the counting and weighing procedures.

Accordingly, in a first aspect, the invention provides a system for controlling articles of equipment for use in surgery, comprising:

(a) articles of equipment for use in surgery, which individually and directly bear a machine readable source of information (b) means for reading the information from the sources on each of the articles: and (c) a computer connected to the reading means for recording information obtained from the information source by the reading means.

In another aspect, the invention provides a method of controlling articles of equipment during surgery, each article directly bearing a machine readable information source, the method comprising reading information from the source on each of the articles using a machine, and recording the information in a computer.

The articles of equipment which may be controlled using the technique of the present invention may be formed from absorbent material. For example, they may be swabs. The technique of the invention is also applicable to articles of equipment such as surgical instruments, which may be formed from metallic or non-metallic materials. The technique is also applicable to sutures which are for use in surgery.

The technique of the present invention generally involves, applying the machine readable information source directly to the articles of equipment, rather than to packets in which the articles are packaged before or after they are sterilised. The provision of the machine readable information source directly on the articles allows the articles to be counted using the indicia reading means not only before use in surgery, but also after use in surgery. Preferably, the machine readable information source is optically readable, as in the case of, for example, a bar code, although other forms of information source such as radio responders and magnetic devices may be used. For example, a bar code may be provided on a strip of a bio-compatible material. A suitable material might be a fabric or a paper, which may be covered with a layer of a polymeric film. A suitable polymer might be a silicone polymer. A suitable coated bar code is that sold by Computype Ltd.

A strip of material on which information is provided, for example in the form of a bar code, may be attached to an article by means of an adhesive. The adhesive will be required to be waterproof and bio-compatible. The strip of material may be attached to certain types of articles, particularly articles formed from fabric of paper, by stitching. This will be possible with many articles formed from absorbent material. When an article consists of more than one layer of material and an outer layer is at least partially transparant for the purpose of reading the indicia, the strip may be located between layers of the article.

The control technique provided by the present invention has several advantages over the manual technique which has been used to date. For example, the use of a computer connected to means for reading information from the articles increases the accuracy with which the articles of equipment are counted and with which the information is recorded. Furthermore information concerning not only the number of articles, but also the nature of identity of the articles can be recorded particularly conveniently using the technique of the invention. The technique can involve the use of significantly less labour than the technique which has been used previously, and the information which is obtained from the articles of equipment and recorded in the computer can provide a permanent record of the equipment which is used during surgery; this information can also be used to control the stock of equipment maintained by a hospital, and can automatically be entered onto a patient's notes, whether for record purposes or for billing purposes.

It is particularly preferred that the system of the invention includes means for weighing the articles of equipment, the weighing means being connected to the computer so that information concerning the weight of the articles can be recorded on the computer. In this embodiment, the system of the invention may be used to calculate automatically the weight of blood and other body fluids which are lost during surgery. By means of the machine readable information on an absorbent article of equipment used during surgery, the article in question can be identified which allows the weight of the article before use to be determined. The computer, to which both the reading means and the weighing means are connected, is then able to calculate the weight gained by the absorbent article of equipment during surgery as a result of absorbtion of body fluid such as blood. Since the articles of equipment are counted at the same time as they are weighed, they may be discarded after they are weighed, and it is not necessary to store them on a rack as part of a subsequent counting procedure. This allows the risk of infection from articles of equipment soaked with body fluids to be reduced.

The system of the invention may also include means for retrieving information from the computer, such as a monitor or a printer. The printer may be used to print a permanent record of the information concerning the articles of equipment used during surgery. The system may also include auxiliary means for entering information into the computer; for example a keyboard may be used to enter information concerning the patient, or concerning articles of equipment for use in surgery, especially surgical instruments.

The system of the invention may also be used to control articles of equipment which bear machine readable information sources, especially bar codes on packets in which they are contained rather than directly on the articles themselves. For example, the system may be used to control sutures which are commonly packaged in packets which contain more than one suture, and in which the packets rather than the sutures bear machine readable information for example in the form of a bar code.

Preferably the articles of equipment are opaque to X-rays, to facilitate location of such articles which have been left in a body cavity after surgery.

Components of the system of the invention, other than the articles of equipment themselves, may be mounted on a trolley so that they can be easily moved from one location to another, for example between operating theatres. Those components may be covered by a sterile cover during surgery so that the system can be operated by a nurse who is required only to contact sterile equipment (a "scrubbed nurse"). Previously used procedures for controlling articles of equipment during surgery required the presence not only of the scrubbed nurse, but also of a nurse who was forbidden from contacting sterile equipment, and who actually maintained the list of equipment in use. The advantages of such reduction in manning levels will be apparent.

BRIEF DESCRIPTION OF THE DRAWINGS

An embodiment of the present invention will now be described, by way of example only, with reference to the accompanying drawings, in which.

DETAILED DESCRIPTION OF THE PRESENTLY PREFERRED EXEMPLARY EMBODIMENT

Figure 1:
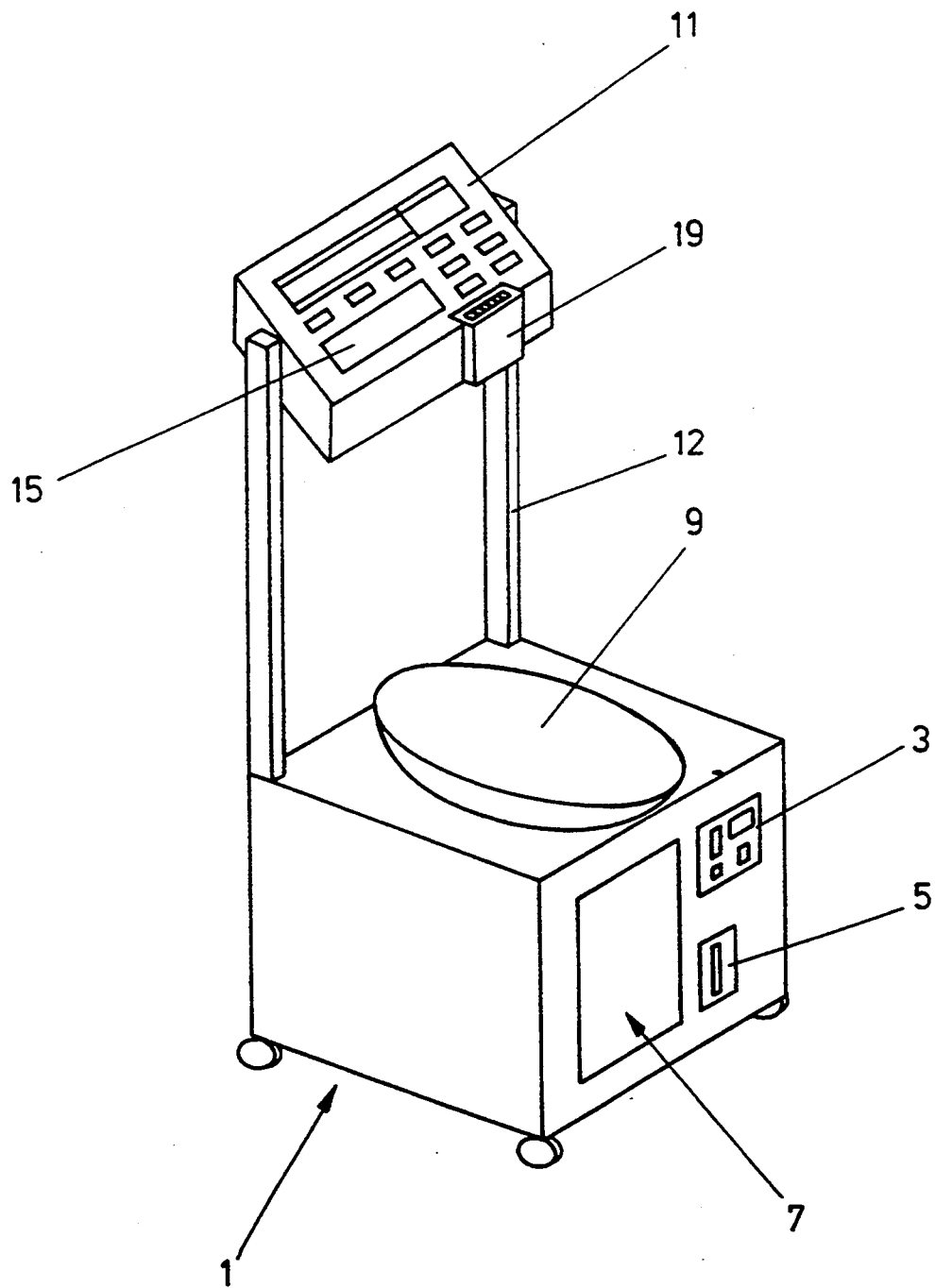
FIG. 1 is an isometric view of a system for controlling articles of equipment for use in surgery.

Referring to the drawings, FIG. 1 shows a system for controlling articles of equipment for use in surgery, which comprises a wheeled trolley unit 1 with a computer B which includes a disk drive 5 mounted towards its base. A printer with a necessary supply of paper is provided in a compartment 7. Scales for weighing articles of equipment are provided above the compartment 7, and information concerning the weight of articles which are weighed by the scales is transmitted directly to the computer 3 for recordal. A bowl 9 is shown on the scales.

Figure 2:
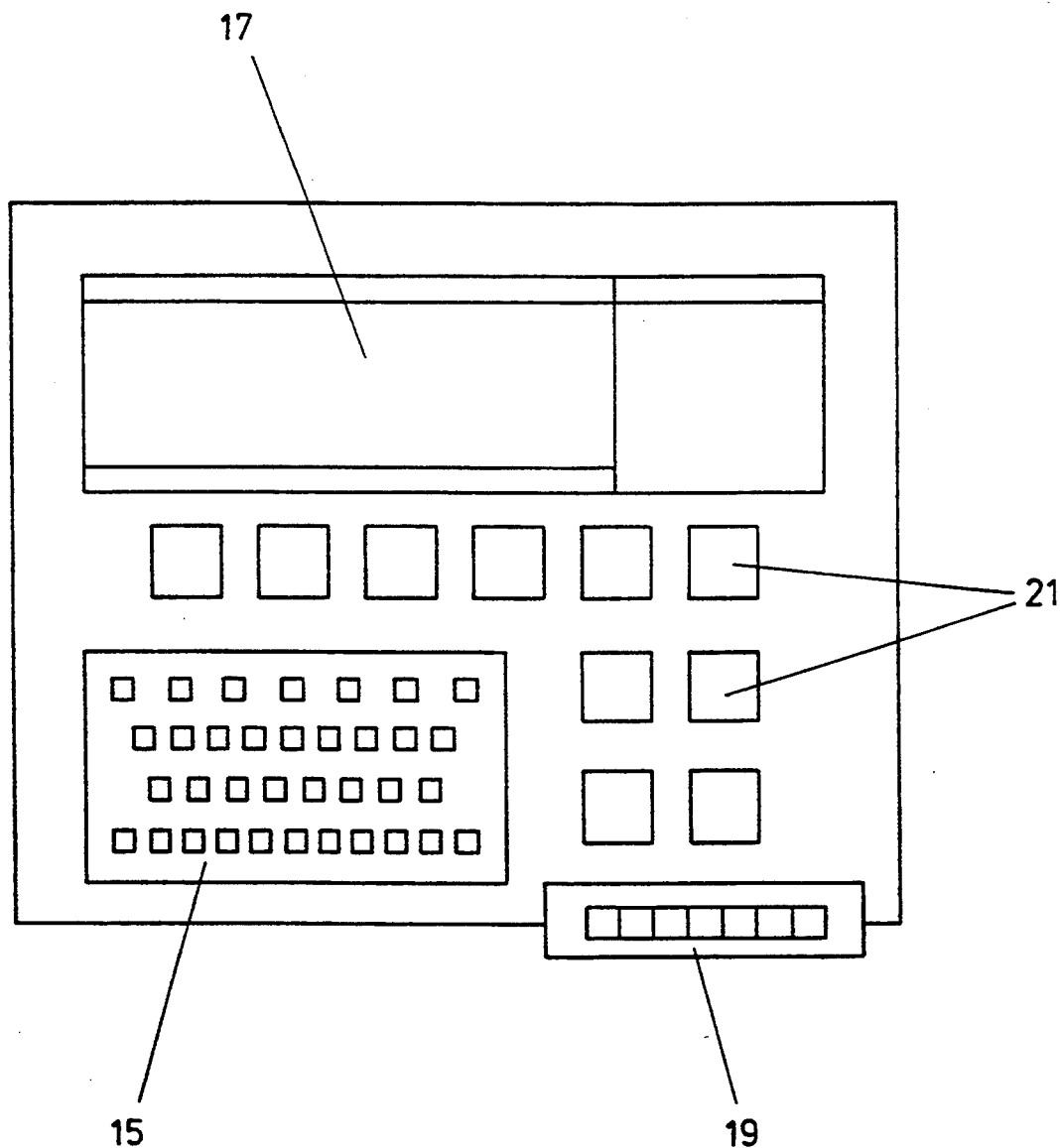
FIG. 2 is a plan view of the console which forms part of the system shown in FIG. 1.

The system includes a console 11 which is mounted onto arms 12 which extend from the base of the trolley unit 1. As shown more clearly in FIG. 2, the console includes a keyboard 15, a monitor 17, through which information recorded in the computer can be displayed, and a bar code reader 19.

The monitor 17 is divided into sections in which the following information can be set out:
theatre identification
date and time
lists of articles of equipment
status information such as fluid loss monitored through scales
input area, reflecting information put into computer through keyboard The keyboard may include "soft keys", 21, which can be arranged for convenience to serve specialised functions during the operation.

I claim:

1. A system for monitoring articles of equipment for use in surgery and recovery after such use, comprising:
   (a) articles of equipment for use in surgery, which individually and directly bear a machine readable source of identifying information;
   (b) reading means (19) for reading the information from the sources on each of the articles both before and after use thereof; and
   (c) a computer (3) connected to the reading means for recording information obtained from the information source by the reading means and for comparing or matching information obtained before use of an article with information obtained after such use.

2. A system as claimed in claim 1, in which the information is optically readable.

3. A system as claimed in claim 1 or claim 2, in which the information is provided on a strip of material which is bio-compatible.

4. A system as claimed in claim 3, in which the information is provided on a strip of fabric or paper, which is covered with a polymeric film.

5. A system as claimed in claim 4, in which the polymeric film comprises a silicone polymer.

6. A system as claimed in claim 1, in which at least some of the articles of equipment are formed from an absorbent material.

7. A system as claimed in claim 6, in which at least some of the articles of equipment are swabs.

8. A system as claimed in claim 1, in which at least some of the articles of equipment are surgical instruments.

9. A system as claimed in claim 1, in which at least some of the articles of equipment are opaque to X-rays.

10. A system as claimed in claim 1, which includes means for weighing the articles of equipment, the weighing means being connected to the computer (3) so that information concerning the weight of the articles can be recorded on the computer.

11. A system as claimed in claim 1 which includes means through which information can be retrieved from the computer.

12. A system as claimed in claim 1 and further comprising at least one non-recoverable article of equipment for use in surgery, which individually and directly bears a machine readable information source readable by the reading means before use of the non-recoverable article.

13. A system as claimed in claim 12, in which the said non-recoverable article is a suture.

14. A method of monitoring articles of equipment used during surgery and recovered after such use, each article directly bearing a machine readable information source, the method comprising reading information from the source on each of the articles both before and after use thereof using a machine, recording the information in a computer, and comparing or matching, by means of the computer, information obtained before use of an article with information obtained after such use.

15. A method as claimed in claim 14, in which means are provided for weighing the articles of equipment, the weighing means being connected to the computer, the method including the steps of weighing at least some of the articles of equipment before and after use in surgery, and recording information concerning the weight of those articles in the computer.

16. A method as claimed in claim 13, which uses a system for monitoring articles of equipment for use in surgery and recovery after such use, comprising:
   (a) articles of equipment for use in surgery, which individually and directly bear a machine readable source of identifying information;
   (b) reading means (19) for reading the information from the sources on each of the articles both before and after use thereof; and
   (c) a computer (3) connected to the reading means for recording information obtained from the information source by the reading means and for comparing or matching information obtained before use of an article with information obtained after such use.

* * * * *